United States Patent
Noda et al.

(10) Patent No.: US 6,784,998 B1
(45) Date of Patent: Aug. 31, 2004

(54) SHEET-MATERIAL FOREIGN-MATTER DETECTING METHOD AND APPARATUS

(75) Inventors: Yuichi Noda, Kanagawa (JP); Takayuki Kamikura, Kanagawa (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 09/556,392

(22) Filed: Apr. 24, 2000

(30) Foreign Application Priority Data

Apr. 28, 1999 (JP) .......................................... 11-121643

(51) Int. Cl.[7] ............................................... G01N 21/84
(52) U.S. Cl. ..................................... 356/430; 356/429
(58) Field of Search .............................. 356/429, 430, 356/238.1, 238.2; 250/559.01; 382/141, 149

(56) References Cited

U.S. PATENT DOCUMENTS

| | | | | |
|---|---|---|---|---|
| 3,814,946 A | * | 6/1974 | Takahashi et al. ..... | 250/559.45 |
| 4,213,708 A | * | 7/1980 | Lucas ......................... | 356/429 |
| 5,109,236 A | * | 4/1992 | Watanabe et al. ........... | 347/193 |
| 5,642,553 A | * | 7/1997 | Leifeld ..................... | 356/237.2 |
| 5,949,550 A | * | 9/1999 | Arndt et al. ................. | 356/430 |

FOREIGN PATENT DOCUMENTS

| | | |
|---|---|---|
| JP | 05018905 | 1/1993 |
| JP | 10123066 | 5/1998 |

* cited by examiner

*Primary Examiner*—Zandra V. Smith
(74) *Attorney, Agent, or Firm*—Rader, Fishman & Grauer PLLC

(57) ABSTRACT

It is an object of the present invention to provide a sheet-material foreign-matter detecting method and apparatus capable of securely detecting foreign matter attached to a sheet material. That is, the foreign matter attached to the sheet material is detected by applying light emitted from a light source to a sheet material, by picking up a light-source image reflected to the surface of the sheet material by image pickup means, and by judging a difference between brightnesses of a reflected image due to a difference between reflectances of the sheet material and the foreign matter.

4 Claims, 3 Drawing Sheets

SHEET-MATERIAL FOREIGN-MATTER DETECTING METHOD AND APPARATUS

BACKGROUND OF THE INVENTION

1. Field of the Invention

The present invention relates to a method and an apparatus for detecting foreign matter of a sheet material formed through, for example, calendering processing.

2. Description of the Prior Art

When the surface of a sheet material formed through calendering processing or the like is covered with a film made of polyethylene or the like, the film has been removed from the sheet material before starting the sheet-material winding step.

However, because the film has a large adhesion, the film is easily cut when the film is removed from the sheet material. If a residual film is left on the sheet material, a trouble occurs in the winding step. Therefore, presence or absence of a residual film has been visually inspected. However, when a film is attached to at the lower side of a sheet material, in a sheet-material carrying line, it may be difficult to find a residual film and thereby, a problem occurs that a reliable inspection cannot be performed. Moreover, because of visual inspection, problems occur that personnel cost for visual inspection increases or operability lowers.

SUMMARY OF THE INVENTION

The present invention is achieved to solve the above problems and its object is to provide sheet-material foreign-matter detecting method and apparatus capable of securely detecting foreign matter attached to a sheet material.

The present invention uses a sheet-material foreign-matter detecting method for detecting whether foreign matter different in reflectance from a sheet material having light reflectivity is attached to the surface of the sheet material while moving the sheet material in a predetermined direction, in which a difference between brightnesses of a reflected image of a light source due to a difference between reflectances of the sheet material and the foreign matter is judged by applying light to a predetermined position of a moving route of the sheet material from a position having a predetermined angle against the surface of the sheet material and picking up a light-source image reflected to the surface of the sheet material by image pickup means.

Thereby, because brightnesses of the light-source reflected image picked up by the image pickup means are different from each other when the foreign matter is attached to the sheet material and when the foreign matter is not attached to the sheet material, the attached foreign matter is detected in accordance with the difference between brightnesses of the reflected image. Therefore, it is possible to always perform a reliable inspection and moreover, automate inspections because foreign matter attached to a sheet material can be securely detected, resulting in an advantage without any personal cost increasing and operability lowering.

Moreover, as for the above method, the light-source reflected image is picked up at a position shifted by a predetermined distance along the surface of the sheet material from a light reflected position along the optical axis of the light source.

Thereby, because a position for picking up the light-source image reflected to the sheet material is shifted from the light reflected position along the optical axis of the light source, a reflected image having a brightness lower than that of a reflected image formed by direct light along the optical axis is detected and a difference between brightnesses of a reflected image due to presence or absence of foreign matter becomes clear. Therefore, it is possible to improve a detection accuracy.

Moreover, it is possible to realize an apparatus having the above functional effect by configuring a sheet-material foreign-matter detecting apparatus for detecting whether foreign matter different in reflectance from a sheet material having light reflectivity is attached to the surface of the sheet material while moving the sheet material in a predetermined direction, by a light source for emitting light to a predetermined position of a moving route of the sheet material from a position having a predetermined angle from the surface of the sheet material, an image pickup means for picking up the light-source image reflected to the surface of the sheet material, and a judging means for performing judgement in accordance with a difference between brightnesses of the light-source reflected image due to a difference between reflectances of the sheet material and the foreign matter.

Moreover, in the above configuration, by shifting a position for picking up the light-source reflected image in the sheet material by a predetermined distance from a light reflecting position along the optical axis of the light source, it is possible to clarify a difference between brightnesses of a reflected image due to presence or absence of foreign matter similarly to the above description.

Furthermore, in the above configuration, by configuring the judging means by image processing means for image-processing the data picked up by the image pickup means and detecting whether the brightness of a predetermined area of processed images including the light-source reflected image becomes a predetermined value or less, the brightness of the predetermined area including the light-source reflected image which is image-processed is judged. Therefore, the brightness is not influenced by light reflected from areas other than the predetermined area. Therefore, it is possible to further improve a detection accuracy.

DESCRIPTION OF THE PREFERRED EMBODIMENT

An embodiment of the present invention will be described below.

The foreign-matter detecting apparatus of this embodiment detects whether or not foreign matter 2 having a reflectance lower than that of a sheet material 1 having light reflectivity is attached to the surface of the material 1 while moving the sheet material 1 by a conveyer 3 in a predetermined direction. The sheet material 1 is a calender material such as a gum sheet or the like. The foreign matter 2 is a film obtained by embossing polyethylene or the like.

Figure 1:
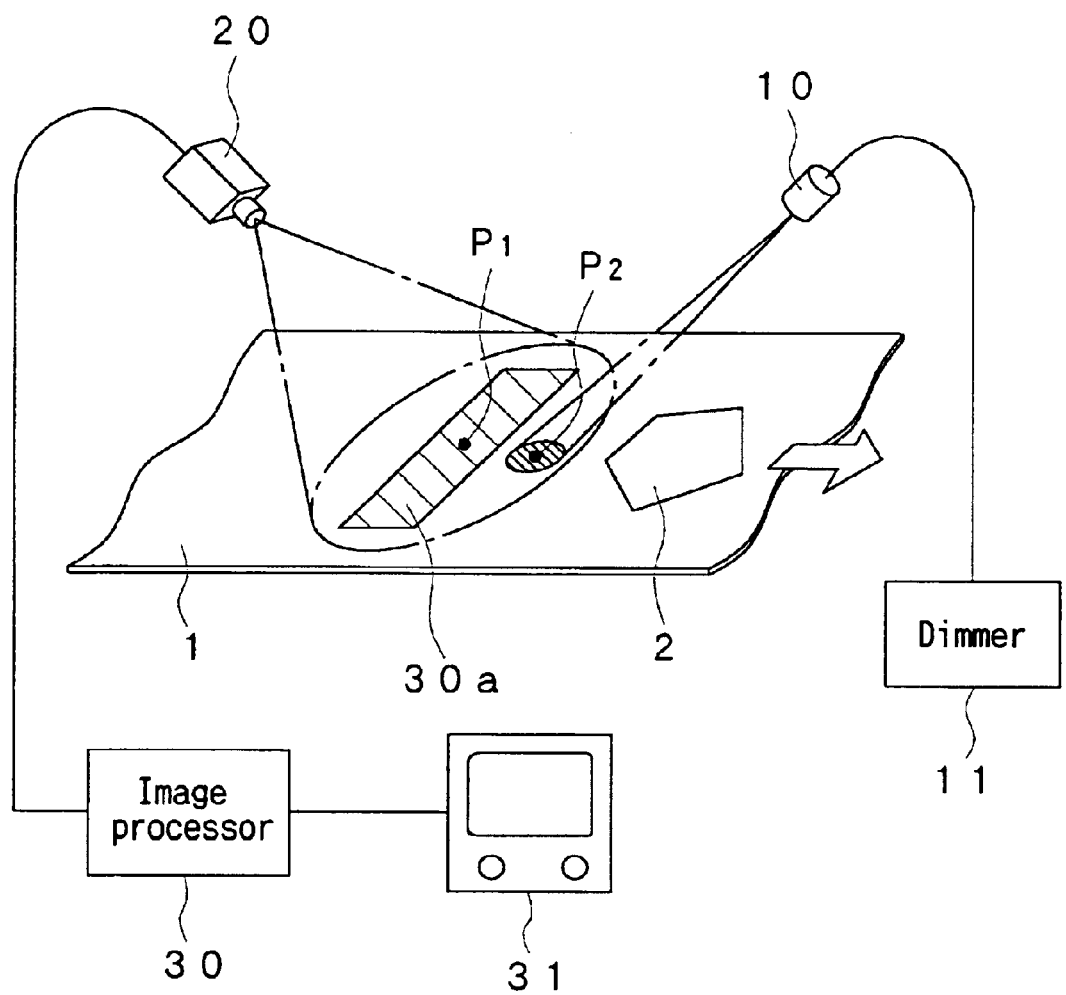
FIG. 1 is a general block diagram of a foreign-matter detecting apparatus showing an embodiment of the present invention.
Figure 2:
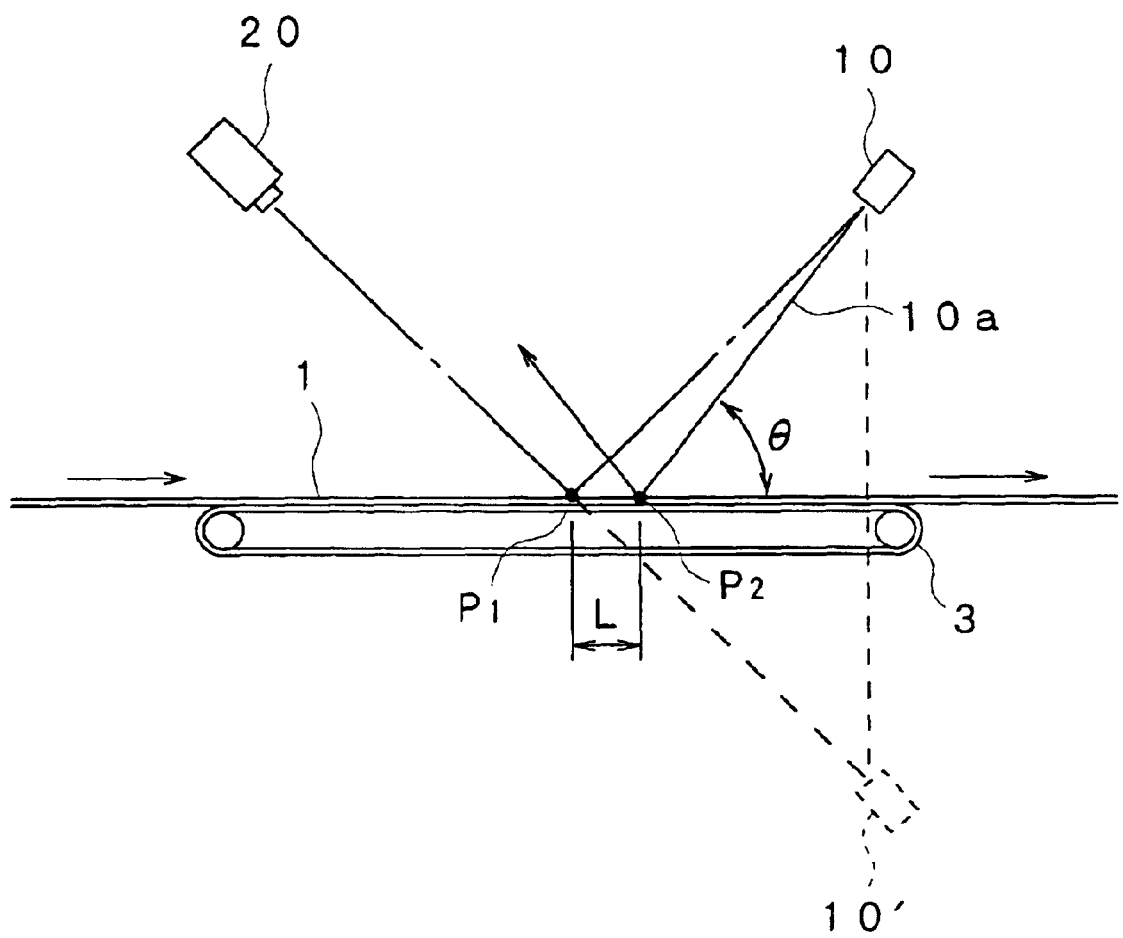
FIG. 2 is a side view of an essential portion of a foreign-matter detecting apparatus.

That is, the foreign-matter detecting apparatus shown in FIG. 1 is configured by a light source 10 for applying light to the surface of the sheet material 1, a CCD camera 20 for picking up an image of the light source 10 reflected on the surface of the sheet material 1, and an image processor 30 for judging attached foreign matter 2 by image-processing the data picked up by the CCD camera 20.

The light source 10 is configured by setting a PL filter to a halogen lamp so as to apply light to a predetermined position of a moving route of the sheet material 1 from a position tilting by an angle θ from the surface of the sheet material 1. Moreover, brightness of the light source 10 can be optionally adjusted by a dimmer 11.

The CCD camera 20 is set to a position almost symmetric to the light source 10 so as to pick up an image of the light source 10 reflected to the surface of the sheet material 1. In this case, a pickup position P1 of a reflected image 1a of the light source 10 on the sheet material 1 is shifted by a distance L in the moving direction of the sheet material 1 from a reflection position P2 of the light along the optical axis 10a of the light source 10.

The image processor 30 sets a predetermined detection area 30a in an image pickup range of the CCD camera 20 so that the pickup position P1 of the reflected image 1a of the light source 10 is included in the detection area 30a but the reflection position P2 of the light along the optical axis 10a of the light source 10 is not included in the area 30a. That is, the image processor 30 operates a not-illustrated warning lamp or buzzer when the brightness of the detection area 30a becomes equal to or less than a predetermined threshold value. Moreover, the reflected image 1a of the light source 10 is always displayed by a monitor 31.

Figure 3A:
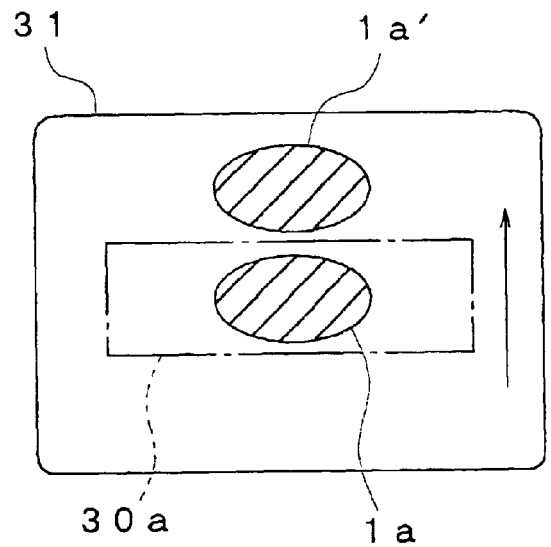
FIGS. 3A and 3B are illustrations showing monitor screens.
Figure 3B:
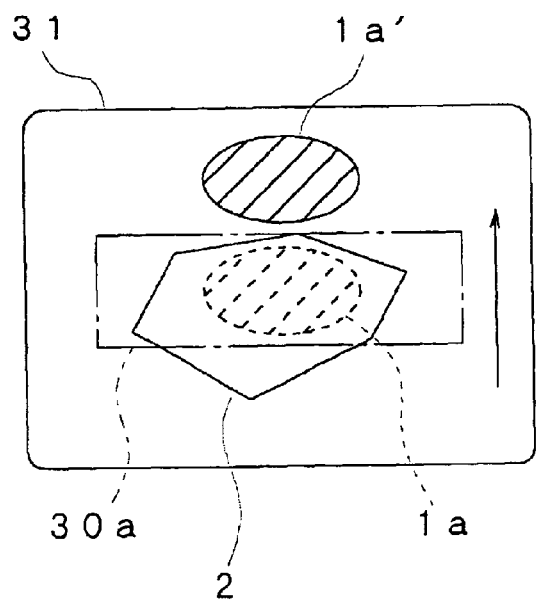

In the sheet-material foreign-matter detecting apparatus configured as described above, light of the light source 10 is applied to the sheet material 1 moved by the conveyer 3, the reflected image 1a of the light source 10 (a virtual image 10 of the light source 10 due to mirror effect of the sheet material 1) being picked up by the CCD camera 20. In this case, as shown by the monitor screen in FIG. 3A, the reflected image 1a of the light source 10 is displayed in the detection area 30a. Moreover, because a reflected image 1a' of the light along the optical axis 10a of the light source 10 is displayed at a position slightly shifted from the detection area 30a, it is not influenced by reflected light other than that of the detection area 30a. Then, when the foreign matter 2 is attached to the surface of the sheet material 1 and enters the detection area 30a as shown by the monitor screen in FIG. 3B, the brightness of the reflected image 1a of the light source 10 lowers or the reflected image 1a disappears because the reflectance of the foreign matter 2 is lower than that of the sheet material 1. Thereby, lowering of the brightness in the detection area 30a is detected by image processing means 30 and it is judged that the foreign matter 2 is attached to the sheet material 1.

Thus, according to the foreign-matter detecting apparatus of this embodiment, light from the light source 10 is applied to the sheet material 1 and the reflected image 1a of the light source 10 reflected on the surface of the sheet material 1 is picked up by the CCD camera 20 to judge the difference between brightnesses of the reflected image 1a due to a difference between reflectances of the sheet material 1 and the foreign matter 2. Therefore, it is possible to securely detect the foreign matter 2 attached to the sheet material 1 and always perform a reliable inspection. Moreover, because inspections can be automated, advantages are obtained that the personnel cost does not increase and the operability does not deteriorate. Furthermore, because a pickup position P1 of the reflected image 1a of the light source 10 on the sheet material 1 is shifted by a predetermined distance L from a reflection position P2 of the light along the optical axis 10a of the light source 10, it is possible to detect the reflected image 1a having a brightness lower than that of the reflected image 1a' formed by direct light along the optical axis 10a and clarify the difference between brightnesses of the reflected image 1a due to presence or absence of the foreign matter 2. In this case, because the reflected image 1a' of the light along the optical axis 10a of the light source 10 is not included in the detection area 30a, the reflected image 1a is not influenced by reflected light other than the light from the detection area 30a and it is possible to further improve a detection accuracy.

Though the above embodiment uses only one light source 10, it is permitted to arrange a plurality of light sources 10 in the width direction of the sheet material 1 when the sheet material 1 has a large width. Moreover, by properly adjusting the brightness of the light source 10, it is possible to make the reflected image 1a' of the light along the optical axis 10a of the light source 10 a detected object. Furthermore, for the above embodiment, a case is described in which the foreign matter 2 lower than the sheet material 1 in reflectance is detected. However, it is also possible to apply the present invention to a case of detecting foreign matter having a reflectance higher than that of a sheet material when the foreign matter and the sheet material have reflectances different from each other.

What is claimed is:

1. A sheet-material foreign-matter detecting method for detecting whether or not a foreign matter light-reflecting surface of foreign matter is different in reflectance from a light-reflecting surface of a sheet material having light reflectivity, the foreign matter being attached to the light-reflecting surface of the sheet material while moving the sheet material in a predetermined direction, comprising the steps of:

applying light to a predetermined position on the light-reflecting surface of a moving route of the sheet material from a position having a predetermined angle from the light-reflecting surface of the sheet material;

picking up as a virtual image of a light source a light-source image reflected from the light-reflecting surface of the sheet material by image-pickup means; and judging a difference between brightnesses of the light-source reflected image due to a difference between reflectances of the light-reflecting surface of the sheet material and the foreign matter light-reflecting surface, wherein a light-source image reflected at a position shifted by a predetermined distance along the light-reflecting surface of the sheet material from a reflection position of the light extending along an optical axis of the light source is picked up.

2. A sheet-material foreign-matter detecting apparatus for detecting whether a foreign matter light-reflecting surface of foreign matter is different in reflectance from a light-reflecting surface of a sheet material having light reflectivity, the foreign matter being attached to a light-reflecting surface of the sheet material while moving the sheet material in a predetermined direction, comprising:

a light source for applying light to a predetermined position on the light-reflecting surface of a moving route of the sheet material from a position having a predetermined angle from the light-reflecting surface of the sheet material;

an image pickup means picking up as a virtual image of a light source a light-source image reflected from the light-reflecting surface of the sheet material; and a judging means for judging a difference between brightnesses of a light-source reflected image due to a difference between reflectances of the light-reflecting surface of the sheet material and the foreign matter light-reflecting surface, wherein a pickup position of a light-source reflected image on the light-reflecting surface of the sheet material is shifted by a predetermined distance along the light-reflecting surface of the sheet material from a reflection position of the light extending along the optical axis of the light source.

3. A sheet-material foreign-matter detecting apparatus for detecting whether foreign matter different in reflectance from a sheet material having light reflectivity is attached to the surface of the sheet material while moving the sheet material in a predetermined direction, comprising:

a light source for applying light to a predetermined position of a moving route of the sheet material from a position having a predetermined angle from the surface of the sheet material;

an image pickup means picking up a light-source image reflected from the surface of the sheet material; and a judging means for judging a difference between brightnesses of a light-source reflected image due to a difference between reflectances of the sheet material and the foreign matter, wherein said judging means is configured by image processing means for image-processing the data picked up by image pickup means and detecting whether or not the brightness of a predetermined area of a processed image including a light-source reflected image becomes a predetermined value or less.

4. A sheet-material foreign-matter detecting apparatus for detecting whether foreign matter different in reflectance from a sheet material having light reflectivity is attached to the surface of the sheet material while moving the sheet material in a predetermined direction, comprising:

a light source for applying light to a predetermined position of a moving route of the sheet material from a position having a predetermined angle from the surface of the sheet material;

an image pickup means picking up a light-source image reflected from the surface of the sheet material; and a judging means for judging a difference between brightnesses of a light-source reflected image due to a difference between reflectances of the sheet material and the foreign matter, wherein a pickup position of a light-source reflected image on the sheet material is shifted by a predetermined distance along the surface of the sheet material from a reflection position of the light extending along the optical axis of the light source and said judging means is configured by image processing means for image-processing the data picked up by image pickup means and detecting whether or not the brightness of a predetermined area of a processed image including a light-source reflected image becomes a predetermined value or less.

* * * * *